United States Patent [19]

Nafziger et al.

[11] Patent Number: 5,118,495
[45] Date of Patent: Jun. 2, 1992

[54] QUICK-DRYING NAIL COATING METHOD AND COMPOSITION

[75] Inventors: Michael D. Nafziger, Mesa; Roger L. Davis; Vivian B. Valenty, both of Tempe, all of Ariz.

[73] Assignee: Lifetime Cosmetics, Inc., Dallas, Tex.

[21] Appl. No.: 535,596

[22] Filed: Jun. 11, 1990

Related U.S. Application Data

[63] Continuation-in-part of Ser. No. 394,200, Aug. 15, 1989, and a continuation-in-part of Ser. No. 235,349, Aug. 23, 1988, abandoned.

[51] Int. Cl.$^5$ .................. A61K 7/043; C09D 101/08; C09D 133/10; C08K 1/18
[52] U.S. Cl. .................. 424/61; 427/54.1; 524/35; 524/560
[58] Field of Search .................. 427/54.1; 424/61

[56] References Cited

U.S. PATENT DOCUMENTS

| | | | |
|---|---|---|---|
| 2,262,274 | 11/1941 | Fingerlin | 34/202 |
| 2,374,472 | 4/1945 | Corbett | 34/202 |
| 3,928,113 | 12/1975 | Rosenberg | 156/344 |
| 4,126,675 | 11/1978 | Boulogne et al. | 424/61 |
| 4,596,260 | 6/1986 | Giuliano | 132/73 |

*Primary Examiner*—Thurman K. Page
*Assistant Examiner*—E. J. Webman
*Attorney, Agent, or Firm*—Antonio R. Durando; Harry M. Weiss

[57] ABSTRACT

A photo-reactive nail polish coating composition that cures quickly upon exposure to low levels of ultraviolet radiation. Compatible with any commercially available nail polish of any color and removable by standard acetone-based polish removers. Also compatible with every day chores because insoluble in water. The composition is not phototoxic and has very low potential for skin irritation or sensitization. The photo-reactive coating is applied over the wet nail polish and then irradiated with safe dosages of ultraviolet radiation, causing the nail polish to dry in a few minutes.

34 Claims, No Drawings

QUICK-DRYING NAIL COATING METHOD AND COMPOSITION

RELATED APPLICATIONS

This application is a continuation-in-part of U.S. application Ser. No. 394,200, filed Aug. 15, 1989, copending, and of U.S. application Ser. No. 235,349, filed Aug. 23, 1988, abandoned.

BACKGROUND OF THE INVENTION

1. Field of the Invention

This invention pertains to the general field of rapidly drying coatings for lacquers and enamels applied to human nails. In particular, the invention concerns a new composition and method for its application which provide a smooth, hard and glossy coating that cures in minutes and is easily removable by commercial nail polish removers.

2. Background of the Invention

Nail polish, lacquers and enamels comprise a class of products regularly used by modern women as part of their beauty care regimen. Enamels are available in a multitude of colors and it is not uncommon for women to strip and reapply nail enamels several times a week in order to match their wardrobe and makeup. This process is time consuming because three to four different layers of coating must be applied and allowed to air dry. Typically, a first layer of colorless base coat is applied, then two layers of color enamel and, finally, a layer of colorless enamel for gloss and protection. During the drying period, which can take as long as several hours, women have to refrain from tasks that might cause them to mar this painstakingly, and sometimes expensively, applied nail polish. Simple operations, such as opening a car door or extracting keys from a purse, can quickly ruin freshly applied fingernail enamel. Thus, in effect, they are prevented from using their hands in any normal everyday activity while the polish is drying. This is especially burdensome for salon customers who need to be able to function normally immediately after receiving a manicure.

Realizing the burden that air drying methods put on people with freshly manicured hands, devices have been developed to try and expedite the drying process. See, for example, U.S. Pat. No. 2,262,274 to Fingerlin (1941) and U.S. Pat. No. 2,374,472 to Corbett (1945). These devices consist generally of a box-like dryer that blows or circulates hot or cold air on the nail's surface for a specified period of time. However, these devices can only dry the surface of the top coating on the nail and do not cause any drying underneath. Consequently, additional exposure to air is required to dry the lower coats of nail polish and in the meantime a manicure can be easily ruined if the nail's surface comes into contact with any hard surface. As a result, nail polish wearers still have to use their hands cautiously for several hours after application in order not to ruin the product of a manicure.

U.S. Pat. No. 3,896,014 and U.S. Pat. No. 3,928,113 to Rosenberg (1975) disclose a process for coating nails comprising the steps of applying a water soluble base coat to the nails, allowing the base coat to dry, then applying a photocurable nail lacquer and curing the lacquer by exposing it to sufficient amounts of radiation. The inventive purpose behind this patent was to try to develop a nail coating that could be removed by water instead of an acetone based commercially available nail polish remover. Accordingly, the nail lacquer was specifically designed for a water soluble base coat, and commercially available nail polishes could not be used in the process. The water soluble base coat that rendered the photocured composition strippable also made the cured film incompatible with daily human functions such as hand and dish washing, bathing, and all other activities involving the immersion of nails in water.

U.S. Pat. No. 4,596,260 to Giuliano (1986) discloses a process of applying a photocurable coating to an artificial nail tip whereby upon exposure to suitable radiation the coating hardens to give the appearance of a natural nail. As it consists of a polyfunctional polymer to which the monomer is crosslinkable, the photocurable coating is very difficult to remove if applied to commonly used nail polishes.

Thus, while these references are relevant to show the general state of the art, they are not directed to the inventive purpose behind the subject invention, which is to rapidly dry a protective coat that can be applied on any commercially available nail polish, lacquer and enamel. Several commercial products have already been introduced that promise a reduction of the drying time of nail coatings. These products include silicone and mineral oils, which provide a slippery surface to the enamel and thus render it non-tacky; but they leave the solvents in place and do not harden the enamel. Also employed are cyclic siloxanes and other low boiling liquids that dry the top surface of the enamel as they evaporate with some of the solvents near the surface. The problem here is that the bulk of the multilayer enamel coating is left laden with solvent and still takes hours to dry and harden.

Infrared lamps, which aid the volatilization of the solvents in the enamel by increasing its temperature, reduce the drying time to about 30 minutes. This is still unsatisfactory, though, for today's growing number of working women who have to juggle their time between a job and housework.

Thus, a method that will further reduce the drying time of multilayer enamel coatings is still needed and it could be expected to have great commercial value in the cosmetics industry. The ultraviolet light apparatus and method described in the copending application referenced above are directed to this specific need.

SUMMARY OF THE INVENTION

An object of the present invention is to provide an ultraviolet photo-reactive nail coating composition and method that utilize safe dosages of ultraviolet radiation to polymerize monomer substances in the coating.

Another object of the invention is to provide a photopolymerizable nail coating composition and method that dries over multiple coats of nail enamels within three minutes of exposure to a low intensity ultraviolet lamp with a long wavelength spectral output.

A further object is to provide a photo-polymerizable composition and method that are compatible with the majority of commercially available nail polish, lacquers and enamels.

Yet another object is to provide a photo-polymerizable composition that is not phototoxic and with very low skin irritation and sensitizing potential.

Finally, a goal of the invention is to provide a photopolymerizable composition that after curing by ultraviolet light is still easily removable by means of commercially available nail polish removers.

Presently, in nail salons and homes around the world, nail polish is applied in a three step process. First, a base-coat is used to fill ridges in the nail and to prevent the colored polish or enamel, applied in step two, from staining the natural nail. Second, two coats of colored polish or enamel are applied. Two coats are usually used in order to provide an opaque and colorful finish. Third, a clear top coat of lacquer is applied to protect the lower layers, applied in step two, to give the nail a prominent shine and provide extended wear.

The present invention provides a coating for nails that is applied as the top coat in step three. Like present day top coats, this coating is clear, it imparts a prominent shine, and also provides extended wear. Unlike present day top coats, the coating is photo-reactive. Thus, after this coating has been applied as a top coat, the present invention also requires a source of ultraviolet radiation, in safe dosages, to irradiate the nail and cause the top coat to react, resulting in the nail polish or enamel underneath drying within a few minutes. The required apparatus is described in copending application Ser. No. 394,200.

The photocuring of the top coat renders the multilayer enamel system dry to the touch immediately after exposure to ultraviolet light, as described in the copending application. The coat is readily resistant to marring by actions such as rubbing with fingertips and hitting by blunt objects. After 5-15 minutes, it is essentially rockhard, as demonstrated by its resistance to marring when scraped with fingernails.

These and other objects, features and advantages of the present invention, as well as details of the preferred embodiment thereof, will be more fully understood from the following description.

DETAILED DESCRIPTION OF THE PREFERRED EMBODIMENT

Nail enamels are generally composed of resins, pigments, dyes, plasticizers, and solvents. Mixtures of low and medium boiling solvents are used to control the rate of evaporation. A high boiling solvent slows the drying process but produces a glossier film; therefore, the drying time of an enamel depends to a large extent on the solvent system. It is easily obvious to a person skilled in the art that one can speed up the enamel's drying time by substituting polymerizable liquid monomers for the solvent system (i.e., the liquid monomers act as the solvent system for the solid components of the enamel). The enamel is then dried and hardened by polymerization of the liquid monomers using a catalytic system that is triggered by heat or light.

Such a method of nail coating, formulated into enamels with a variety of dyes and pigments, constitutes a new family of nail enamels that could make current products obsolete. The problem with such systems is that the coatings are difficult to remove. U.S. Pat. No. 3,928,113, described above, offered a solution by the use of a water soluble base coat before applying the photocurable nail enamel. As opposed to that method, the coating of this invention is resistant to the usual tasks of dish washing, hand washing, or other chores involving the contact of fingers with hot water.

Furthermore, this prior art is different from the present invention in composition, as well as in function or use. U.S. Pat. No. 3,928,113 claims a method of coating human nails whereby a water soluble or swellable base coat is first applied, followed by a photocurable pigmented or unpigmented polymer composition to provide a multilayer nail enamel that is removable when soaked in hot water. Our invention does not utilize a water soluble or swellable basecoat because, as explained above, that approach is not compatible with normal every day tasks that involve soaking the hands in warm or hot water. In addition, the photocurable composition of this prior art also serves as the principal enamel and therefore is pigmented in most cases. Our invention is clear and unpigmented for use as a topcoat on any commercially available nail enamel. Finally, from a compositional point of view, this prior art discloses a polythiol as an essential ingredient in the claimed composition. Our invention does not require a polythiol.

U.S. Pat. No. 4,596,260 utilizes known photopolymerizable compositions for adhering preformed artificial nail tips to natural nails. This composition also differs from our invention not only in function, but in formulation as well. That patent claims a composition wherein a monomer is crosslinkable with the required polymer component which is claimed to be a low molecular weight acrylated urethane oligomer free of reactive isocyanate groups. Such a reactive polymer is not required in our present invention.

Furthermore, that patent describes in detail the ultraviolet lamp which is suitable for photocuring according to the claimed method. Although no specification on the lamp intensity is provided, an example is given with a lamp having 100 watt capacity. Our present invention utilizes a lamp that is of low intensity (i.e., less than 10 watts). As a result the lamp used in our invention is safer and less annoying to the eyes, as claimed in copending application Ser. No. 394,200.

In general, the prior art, which include both the patent literature and polymer texts, is rich with references to photocurable compositions. Typically, these compositions include at least one suitable polyfunctional polymer or oligomer, a photoinitiator and a liquid monomer in which the various other ingredients are soluble, the monomer being crosslinkable with the polyfunctional polymer in the presence of actinic radiation (e.g., ultraviolet radiation) to form a plastic film. As is understood in the art, the degree of firmness is in part dependent upon the degree of crosslinking and one skilled in the art understands that varying the ratio of monomer to polymer can provide greater or lesser firmness or rigidity of the product. Polyfunctional monomers are also used in prior art and the ratio of polyfunctional monomer to monofunctional monomer is varied as well to provide greater or lesser firmness or rigidity to the product. Moreover, the reactivity of the functionality itself affects the curing rate and also determines the firmness or rigidity of the product. For example, acrylates are more reactive and form harder coatings than the corresponding methacrylates.

On the bases of prior art knowledge, usable photoreactive compositions for use in conjunction with an ultraviolet rapid-dry device have been developed and are described in the copending application. As mentioned above, for example, it was found that acrylates react faster than methacrylates and result in harder photocured systems, but methacrylates have lower skin irritation and sensitization potential. Accordingly, compositions based on methacrylate functionality alone are preferable and have become the focus of our research. In the course of further investigation related to the present invention, a further welcomed but unexpected observation was made that a totally methacrylate monomer system, in the presence of nitrocellulose, cures hard within three minutes of exposure to a low intensity, long wave ultraviolet lamp. Also to our surprise, we found that a methacrylate system consisting of only monofunctional monomers, instead of the difunctional monomers taught by prior art, cured into a hard coat over three layers of nail enamel within three minutes of exposure to our prototype lamp. As expected, such systems have lower skin irritating properties than a similar system comprised of an acrylate monomer.

Accordingly, the photo-reactive coating of this invention is comprised of solvents, a primary film-forming resin, photocurable monomers (mono or difunctional), a photoinitiator and an inhibitor. As these ingredients are commonly found in nail coating products, one skilled in the art would readily understand the purpose for each in the photo-reactive coating. Similarly, the method of mixing and preparation of the resulting composition would be obvious in the art. Consequently, these ingredients and the process of preparation of the resulting product need not be discussed in great detail.

In the preferred embodiment of the coating, the solvents are ethyl acetate or n-butyl acetate, and the primary film former (polymer) is nitrocellulose, which is available commercially in isopropanol as a carrier and wetting agent. The use of these solvents and primary film former permits the removal of the coating by any commercially available acetone based nail polish remover and improves the coating's compatibility with commercially available colored nail enamels and lacquers.

Nitrocellulose is used in concentrations from 5 to 30 percent by weight (preferably from 18 to 22 percent) of the total composition. Correspondingly, as a result of the ratio normally found in commercial products, isopropanol will be present in concentrations varying approximately from 2 to 13 percent by weight. The solvent, whether ethyl acetate or n-butyl acetate, is used in approximately 50 percent greater quantity than nitrocellulose. In any event, the compositions of all ingredients with solvent characteristics may be varied to obtain the desired viscosity of the final product.

Photoreactive monomers are used, either alone or in mixture, in total concentrations between 2 and 55 percent by weight. Optimal concentrations are from 5 to 43 percent by weight of the total composition. In general, we found that dimethacrylate monomers of the following formula are acceptable for practicing this invention:

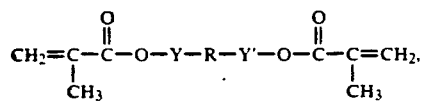

where Y and Y' may be the same or different but can be any hydrocarbyl difunctional radicals with 1–4 carbon atoms; R is any hydrocarbyl difunctional radical with 1–10 carbon atoms; and the Y and Y' radicals may be joined to the R radical by means of any organic group with two free bonds, known to those skilled in the art as linking radicals in which one or two atoms separate R from Y and Y', such as —O—, —NH—, —S—, —CO—, —CH$_2$—, SO, —SO$_2$—, —SO$_2$O—. —NH—CO—, and —NR'—, where R' is an aliphatic monofunctional radical with 1–4 carbon atoms. R may be aliphatic, alicyclic or aromatic.

In particular, we found that the following difunctional methacrylate monomers, together with monofunctional methacrylates according to the total quantities listed above, are particularly suitable in the percentages shown:

| Difunctional Methacrylate Monomer | Weight % Range | Optimal Range |
|---|---|---|
| 1,4 Butanediol dimethacrylate | 0.4–10.0 | 0.5–5.5 |
| 1,3 Butanediol dimethacrylate | 0.4–10.0 | 0.5–5.5 |
| Diurethane dimethacrylate | 0.4–6.0 | 0.4–5.5 |

As mentioned above, though, and most significantly of this invention, we also found that monofunctional methacrylate monomers alone produce a rapidly curing product. Some of these methacrylate monomers and the corresponding ranges of use are given below:

| Monofunctional Methacrylate Monomer | Weight % Range | Optimal Range |
|---|---|---|
| Ethyl methacrylate | 2.0–55.0 | 5.0–43.0 |
| Cyclohexyl methacrylate | 2.0–55.0 | 2.0–20.0 |
| Isobutyl methacrylate | 2.0–55.0 | 5.0–43.0 |
| Methyl methacrylate | 2.0–55.0 | 5.0–43.0 |
| Isobornyl methacrylate | 2.0–25.0 | 2.0–6.0 |
| Furfuryl methacrylate | 2.0–25.0 | 2.0–6.0 |
| Tetrahydrofurfuryl methacrylate | 2.0–25.0 | 2.0–6.0 |

The preferred monomers are methacrylic acid ester monomers, such as ethyl methacrylate or cyclohexyl methacrylate or, preferably, a mixture of the two within the total preferred concentrations listed above. In the place of cyclohexyl methacrylate, furfuryl- and tetrahydrofurfuryl methacrylate have been found to result in a product with comparable curing characteristics. Similarly, isobutyl and methyl methacrylate can be used instead of ethyl methacrylate. Isobornyl methacrylate has been found to perform well in conjunction with diurethane dimethacrylate, with or without ethyl methacrylate. Since ethyl methacrylate acts as a solvent as well as a reactive monomer, its quantity must be adjusted as a function of the other monomers used to provide the appropriate product viscosity.

Any one of several known photoinitiators of the aryl or the alkyl aryl ketone type may be used to practice this invention. For example, these include photoinitiators, such as benzophenone, diethoxyacetophenone, benzil diketal (BDK), as well as other well known products. It was found that 2-hydroxy-2-methyl-1-phenyl-propanone, available, for example, as the product sold by EM Industries, Inc. under the trademark "Darocur 1173," is preferred. The photoinitiator is used in concentrations from 0.5 to 5 weight percent, preferably between 2 and 4 percent of the total composition.

Inhibitors of polymerization are a necessary ingredient of the claimed composition in order to provide shelf stability to the formulation. Useful inhibitors are also well known in the art and include hydroquinone and substituted analogs such as 4-methoxyphenol (MEHQ), either singularly or in combination with antioxidants to suppress yellowing. For example, MEHQ may be used at a concentration of about 25 to 200 ppm in combination with tris-(4-t-butyl-3-hydroxy-2,6-dimethylbenzyl)-s-triazine-2,4,6-trione, sold as "Cyanox 1790" (a trademark of American Cyanamid Co.), at 0.25 weight percent of the total composition.

Other ingredients may also be added to impart specific desirable function. For example, surfactants like sorbitan trioleate to improve homogeneity, plasticizers like dibutyl phthalate to flexibilize the cured coating, slip agents, fragrance or masking agents, and the like.

The following examples list alternative formulations of the preferred embodiment of the coating according to this invention.

EXAMPLE 1

| Ingredient | Weight Percent |
| --- | --- |
| Nitrocellulose | 19.5 |
| Isopropanol | 8.4 |
| Ethyl acetate | 27.9 |
| Ethyl methacrylate | 26.7 |
| Cyclohexyl methacrylate | 12.6 |
| "Darocur 1173" | 4.0 |
| MEHQ | 40 ppm |
| "Cyanox 1790" | 0.07 |
| Sorbitan Trioleate | 0.9 |

EXAMPLE 2

| Ingredient | Weight Percent |
| --- | --- |
| Nitrocellulose | 18.3 |
| Isopropanol | 7.9 |
| n-Butyl acetate | 26.2 |
| Ethyl methacrylate | 28.8 |
| Cyclohexyl methacrylate | 13.6 |
| "Darocur 1173" | 4.4 |
| MEHQ | 42 ppm |
| "Cyanox 1790" | 0.02 |
| Sorbitan trioleate | 1.0 |

EXAMPLE 3

| Ingredient | Weight Percent |
| --- | --- |
| Nitrocellulose | 21.8 |
| Isopropanol | 9.4 |
| Ethyl acetate | 31.2 |
| Ethyl methacrylate | 18.5 |
| Cyclohexyl methacrylate | 14.4 |
| "Darocur 1173" | 2.8 |
| MEHQ | 114 ppm |
| "Cyanox 1790" | 0.26 |
| Sorbitan trioleate | 1.0 |
| Dibutyl phthalate | 0.4 |
| Fragrance | 0.2 |

EXAMPLE 4

| Ingredient | Weight Percent |
| --- | --- |
| Nitrocellulose | 18.3 |
| Isopropyl alcohol | 7.9 |
| Hexane | 5.5 |
| Ethyl acetate | 16.5 |
| Ethyl methacrylate | 41.3 |
| 1,4 butanediol dimethacrylate | 2.75 |
| Diurethane dimethacrylate | 2.75 |
| MEHQ | 165 ppm |
| Sorbitan Trioleate | 0.83 |
| Fragrance | 0.55 |
| "Darocur 1173" | 2.75 |

EXAMPLE 5

| Ingredient | Weight Percent |
| --- | --- |
| Nitrocellulose | 14.1 |
| Isopropyl alcohol | 6.0 |
| Ethyl acetate | 19.7 |
| Ethyl methacrylate | 50.4 |
| MEHQ | 129 ppm |
| 1,4 butanediol dimethacrylate | 2.5 |
| Diurethane dimethacrylate | 2.6 |
| "Darocur 1173" | 4.0 |

EXAMPLE 6

| Ingredient | Weight Percent |
| --- | --- |
| Nitrocellulose | 18.0 |
| Isopropyl alcohol | 7.7 |
| Ethyl acetate | 58.3 |
| 1,4 butanediol dimethacrylate | 0.5 |
| Diurethane dimethacrylate | 0.5 |
| Ethyl methacrylate | 12.3 |
| MEHQ | 148 ppm |
| "Darocur 1173" | 2.0 |

EXAMPLE 7

| Ingredient | Weight Percent |
| --- | --- |
| Nitrocellulose | 15.1 |
| Isopropyl alcohol | 6.5 |
| Diurethane dimethacrylate | 2.4 |
| 1,4 butanediol dimethacrylate | 3.96 |
| Isobutyl methacrylate | 1.94 |
| Isobornyl methacrylate | 4.31 |
| Ethyl acetate | 62.5 |
| MEHQ | 43 ppm |
| "Darocur 1173" | 1.62 |

EXAMPLE 8

| Ingredient | Weight Percent |
| --- | --- |
| Nitrocellulose | 20.0 |
| Isopropyl alcohol | 8.6 |
| Diurethane dimethacrylate | 2.9 |
| 1,4 butanediol dimethacrylate | 4.7 |
| Isobornyl methacrylate | 2.3 |
| Cyclohexyl methacrylate | 5.2 |
| Ethyl acetate | 52.0 |
| MEHQ | 26 ppm |
| "Darocur 1173" | 3.1 |

EXAMPLE 9

| Ingredient | Weight Percent |
| --- | --- |
| Nitrocellulose | 15.5 |
| Isopropyl alcohol | 6.7 |
| Diurethane dimethacrylate | 3.5 |
| 1,4 butanediol dimethacrylate | 5.1 |
| Isobutyl methacrylate | 8.9 |
| Ethyl acetate | 57.7 |
| MEHQ | 22 ppm |
| "Darocur 1173" | 1.7 |

EXAMPLE 10

| Ingredient | Weight Percent |
| --- | --- |
| Nitrocellulose | 20.9 |
| Isopropyl alcohol | 8.9 |
| Diurethane dimethacrylate | 3.3 |
| 1,4 butanediol dimethacrylate | 5.4 |
| Ethyl methacrylate | 8.6 |
| Ethyl acetate | 50.7 |
| "Darocur 1173" | 2.1 |

As would be appreciated by one skilled in the art, these chemicals were selected, in part, because they are non-toxic and generally non-photoallergenic.

While the invention has been particularly shown and described with reference to a preferred embodiment thereof, it will be understood by those skilled in the art that changes in form and detail may be made therein without departing from the spirit and the scope of the invention.

What we claim is:

1. A photo-reactive coating for application over and for binding with nail polish upon exposure to ultraviolet radiation, comprising:
   (a) a base resin consisting of nitrocellulose;
   (b) a photo-reactive monomer; selected from the group consisting of dimethacrylates, methacrylates, and mixtures thereof.
   (c) a photoinitiator; and
   (d) an inhibitor to polymerization;
wherein said nitrocellulose is used in concentrations from 5 to 30 percent by weight of the total composition; wherein said photo-reactive monomer is used in concentrations from 2 to 55 percent by eight of the total composition; wherein said photoinitiator is used in concentrations from 0.5 to 5 percent by weight of the total composition; and wherein said inhibitor is used in concentrations from 25 to 200 parts per million.

2. A photo-reactive coating for nail polish for application over and for binding with said nail polish upon exposure to ultraviolet radiation, comprising:
   (a) a base resin consisting of nitrocellulose;
   (b) a photo-reactive monomer;
   (c) a photoinitiator; and
   (d) an inhibitor to polymerization;
wherein said nitrocellulose is used in concentrations from 15 to 30 percent by weight of the total composition; said photo-reactive monomer is used in concentrations from 2 to 55 percent by weight of the total composition and is selected from the group consisting of 1-4 butanediol dimethacrylate, 1-3 butanediol dimethacrylate, diurethane dimethacrylate, ethyl methacrylate, cyclohexyl methacrylate, isobutyl methacrylate, isobornyl methacrylate, furfuryl methacrylate, and tetrahydrofurfuryl methacrylate; said photoinitiator is used in concentrations from 0.5 to 5 percent by weight of the total composition, and said inhibitor is used in concentrations from 25 to 200 parts per million.

3. The coating of claim 1, wherein said photo-reactive monomer is a dimethacrylate monomer of the following general formula

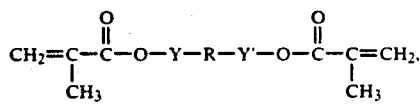

where Y and Y' may be the same or different but can be any hydrocarbyl difunctional radicals with 1-4 carbon atoms; R is any hydrocarbyl difunctional radical with 1-10 carbon atoms; the Y and Y'radicals may be joined to the R radical by means of any organic group with two free bonds, known to those skilled in the art as linking radicals, in which one or two atoms separate R from Y and Y', and R may be aliphatic, alicyclic or aromatic.

4. The coating of claim 2, wherein said photo-reactive monomer is 1-4 butanediol dimethacrylate in concentrations from 0.4 to 10 percent by weight in conjunction with monofunctional methacrylates.

5. The coating of claim 2, wherein said photo-reactive monomer is 1-3 butanediol dimethacrylate in concentrations from 0.4 to 10 percent by weight in conjunction with monofunctional methacrylates.

6. The coating of claim 2, wherein said photo-reactive monomer is diurethane dimethacrylate in concentrations from 0.4 to 6 percent by weight in conjunction with monofunctional methacrylates.

7. The coating of claim 2, wherein said photo-reactive monomer consists of at least one monomer from the class of methacrylic acid ester monomers.

8. The coating of claim 2, wherein said photo-reactive monomer is ethyl methacrylate.

9. The coating of claim 2, wherein said photo-reactive monomer is cyclohexyl methacrylate.

10. The coating of claim 2, wherein said photo-reactive monomer is isobutyl methacrylate.

11. The coating of claim 7, wherein said photo-reactive monomer is methyl methacrylate.

12. The coating of claim 2, wherein said photo-reactive monomer is isobornyl methacrylate.

13. The coating of claim 2, wherein said photo-reactive monomer is furfuryl methacrylate.

14. The coating of claim 2, wherein said photo-reactive monomer is tetrahydrofurfuryl methacrylate.

15. The coating of claim 1, wherein said photoinitiator is selected from the group consisting of benzophenone, diethoxyacetophenone, benzil diketal, and 2-hydroxy-2-methyl-1-phenylpropanone.

16. The coating of claim 15, wherein said photoinitiator is benzophenone.

17. The coating of claim 15, wherein said photoinitiator is diethoxyacetophenone.

18. The coating of claim 15, wherein said photoinitiator is benzil diketal.

19. The coating of claim 1, wherein said inhibitor is hydroquinone.

20. The coating of claim 1, wherein said inhibitor is 4-methoxyphenol hydroquinone.

21. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
| --- | --- |
| nitrocellulose | 19.5 |
| isopropanol | 8.4 |
| ethyl acetate | 27.9 |
| ethyl methacrylate | 26.7 |
| cyclohexyl methacrylate | 12.6 |
| 2-hydroxy-2-methyl-1-phenylpropanone | 4.0 |
| 4-methoxyphenol | 40 ppm |
| tris(4-t-butyl-3-hydroxy-2,6-dimethylbenzyl)-s-triazine-2, | 0.07 |

| Ingredient | Weight Percent |
|---|---|
| 4,6-trione | |
| sorbitan trioleate | 0.9 |

22. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
|---|---|
| nitrocellulose | 18.3 |
| isopropanol | 7.9 |
| n-butyl acetate | 26.2 |
| ethyl methacrylate | 28.8 |
| cyclohexyl methacrylate | 13.6 |
| 2-hydroxy-2-methyl-1-phenylpropanone | 4.4 |
| 4-methoxyphenol | 42 ppm |
| tris(4-t-butyl-3-hydroxy-2,6-dimethylbenzyl)-s-triazine-2,4,6-trione | 0.02 |
| sorbitan trioleate | 1.0 |

23. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
|---|---|
| nitrocellulose | 21.8 |
| isopropanol | 9.4 |
| ethyl acetate | 31.2 |
| ethyl methacrylate | 18.5 |
| cyclohexyl methacrylate | 14.4 |
| 2-hydroxy-2-methyl-1-phenylpropanone | 2.8 |
| 4-methoxyphenol | 114 ppm |
| tris(4-t-butyl-3-hydroxy-2,6-dimethylbenzyl)-s-triazine-2,4,6-trione | 0.26 |
| sorbitan trioleate | 1.0 |
| dibutyl phthalate | 0.4 |
| fragrance | 0.2 |

24. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
|---|---|
| nitrocellulose | 18.3 |
| isopropyl alcohol | 7.9 |
| hexane | 5.5 |
| ethyl acetate | 16.5 |
| ethyl methacrylate | 41.3 |
| 1,4 butanediol dimethacrylate | 2.75 |
| diurethane dimethacrylate | 2.75 |
| 4-methoxyphenol | 165 ppm |
| sorbitan trioleate | 0.83 |
| fragrance | 0.55 |
| 2-hydroxy-2-methyl-1-phenylpropanone | 2.75 |

25. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
|---|---|
| nitrocellulose | 14.1 |
| isopropyl alcohol | 6.0 |
| ethyl acetate | 19.7 |
| ethyl methacrylate | 50.4 |
| 4-methoxyphenol | 129 ppm |
| 1,4 butanediol dimethacrylate | 2.5 |
| diurethane dimethacrylate | 2.6 |
| 2-hydroxy-2-methyl-1-phenylpropanone | 4.0 |

26. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
|---|---|
| nitrocellulose | 18.0 |
| isopropyl alcohol | 7.7 |
| ethyl acetate | 58.3 |
| 1,4 butanediol dimethacrylate | 0.5 |
| diurethane dimethacrylate | 0.5 |
| ethyl methacrylate | 12.3 |
| 4-methoxyphenol | 148 ppm |
| 2-hydroxy-2-methyl-1-phenylpropanone | 2.0 |

27. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
|---|---|
| nitrocellulose | 15.1 |
| isopropyl alcohol | 6.5 |
| diurethane dimethacrylate | 2.4 |
| 1,4 butanediol dimethacrylate | 3.96 |
| isobutyl methacrylate | 1.94 |
| isobornyl methacrylate | 4.31 |
| ethyl acetate | 62.5 |
| 4-methoxyphenol | 43 ppm |
| 2-hydroxy-2-methyl-1-phenylpropanone | 1.62 |

28. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
|---|---|
| nitrocellulose | 20.0 |
| isopropyl alcohol | 8.6 |
| diurethane dimethacrylate | 2.9 |
| 1,4 butanediol dimethacrylate | 4.7 |
| isobornyl methacrylate | 2.3 |
| cyclohexyl methacrylate | 5.2 |
| ethyl acetate | 52.0 |
| 4-methoxyphenol | 26 ppm |
| 2-hydroxy-2-methyl-1-phenylpropanone | 3.1 |

29. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
| --- | --- |
| nitrocellulose | 15.5 |
| isopropyl alcohol | 6.7 |
| diurethane dimethacrylate | 3.5 |
| 1,4 butanediol dimethacrylate | 5.1 |
| isobutyl methacrylate | 8.9 |
| ethyl acetate | 57.7 |
| 4-methoxyphenol | 22 ppm |
| 2-hydroxy-2-methyl-1-phenylpropanone | 1.7 |

30. A photo-reactive coating for application over and for binding with nail polish upon exposure to ultraviolet radiation from an ultraviolet lamp with less than 10 watts of power, comprising the following ingredients in the specified concentrations:

| Ingredient | Weight Percent |
| --- | --- |
| nitrocellulose | 20.9 |
| isopropyl alcohol | 8.9 |
| diurethane dimethacrylate | 3.3 |
| 1,4 butanediol dimethacrylate | 5.4 |
| ethyl methacrylate | 8.6 |
| ethyl acetate | 50.7 |
| 2-hydroxy-2-methyl-1-phenylpropanone | 2.1 |

31. The coating of claim 2, wherein said nitrocellulose is used in concentrations from 18 to 22 percent by weight of the total composition, said photo-reactive monomer is used in concentrations from 5 to 43 percent by weight of the total composition, said photoinitiator is used in concentrations from 2 to 4 percent by weight of the total composition, and said inhibitor is used in concentrations from 25 to 200 parts per million.

32. The coating of claim 3, wherein said dimethacrylate monomer is 1-4 butanediol dimethacrylate in concentrations from 0.5 to 5.5 percent by weight and is used together with a monofunctional methacrylate selected from the group consisting of ethyl methacrylate, cyclohexyl methacrylate, isobutyl methacrylate, methyl methacrylate, isobornyl methacrylate, furfuryl methacrylate, and tetrahydrofurfuryl methacrylate and mixtures thereof in concentrations from 2.0 and 55.0 percent by weight.

33. The coating of claim 3, wherein said dimethacrylate monomer is 1-3 butanediol dimethacrylate in concentrations from 0.5 to 5.5 percent by weight and is used together with a monofunctional methacrylate selected from the group consisting of ethyl methacrylate, cyclohexyl methacrylate, isobutyl methacrylate, methyl methacrylate, isobornyl methacrylate, furfuryl methacrylate, and tetrahydrofurfuryl methacrylate and mixtures thereof in concentrations from 2.0 and 55.0 percent by weight.

34. The coating of claim 3, wherein said dimethacrylate monomer is diurethane dimethacrylate in concentrations from 0.4 to 5.5 percent by weight and is used together with a monofunctional methacrylate selected from the group consisting of ethyl methacrylate, cyclohexyl methacrylate, isobutyl methacrylate, methyl methacrylate, isobornyl methacrylate, furfuryl methacrylate, and tetrahydrofurfuryl methacrylate and mixtures there in concentrations from 2.0 and 55.0 percent by weight.

* * * * *